US00PP32215P2

(12) United States Plant Patent
van Sambeek

(10) Patent No.: US PP32,215 P2
(45) Date of Patent: Sep. 15, 2020

(54) *GAILLARDIA* PLANT NAMED 'DOGAILSPINCOPSUN'

(50) Latin Name: *Gaillardia aristata*
Varietal Denomination: Dogailspincopsun

(71) Applicant: DUMMEN GROUP B.V., De Lier (NL)

(72) Inventor: Ellen van Sambeek, Oegstgeest (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/501,819

(22) Filed: Jun. 11, 2019

(51) Int. Cl.
*A01H 5/02* (2018.01)
*A01H 6/14* (2018.01)

(52) U.S. Cl.
USPC ..... Plt./431
CPC ..... *A01H 6/14* (2018.05)

(58) Field of Classification Search
USPC ..... Plt./431
CPC ..... A01H 6/14
See application file for complete search history.

(56) References Cited

PUBLICATIONS

UPOV hit on *Gaillardia* plant named, 'Dogailspincopsun', QZ PBR 20191124, filed May 3, 2019.*

* cited by examiner

*Primary Examiner* — Anne Marie Grunberg
(74) *Attorney, Agent, or Firm* — C. A. Whealy

(57) ABSTRACT

A new and distinct cultivar of *Gaillardia* plant named 'Dogailspincopsun', characterized by its compact and mounded plant habit; freely branching habit; dense and bushy habit; strong leaves that resist yellowing; early and freely flowering habit; single inflorescences with red and yellow bi-colored ray florets; and good garden performance.

2 Drawing Sheets

Botanical designation: *Gaillardia aristata.*
Cultivar denomination: 'DOGAILSPINCOPSUN'.

BACKGROUND OF THE INVENTION

The present invention relates to a new and distinct cultivar of *Gaillardia* plant, botanically known as *Gaillardia aristata* and hereinafter referred to by the name 'Dogailspincopsun'.

The new *Gaillardia* plant is a product of a planned breeding program conducted by the Inventor in Aalsmeer, The Netherlands. The objective of the breeding program is to create new compact *Gaillardia* plants with numerous attractive inflorescences and healthy leaves.

The new *Gaillardia* plant originated from an open-pollination in July, 2014 of a proprietary selection of *Gaillardia aristata* identified as code number GA13-000001-001, not patented, as the female, or seed, parent with an unknown selection of *Gaillardia aristata* as the male, or pollen, parent. The new *Gaillardia* plant was discovered and selected by the Inventor as a single flowering plant from within the progeny of the stated cross-pollination in a controlled environment in Aalsmeer, The Netherlands in July, 2015.

Asexual reproduction of the new *Gaillardia* plant by vegetative terminal cuttings in Aalsmeer, The Netherlands, since August, 2015 has shown that the unique features of this new *Gaillardia* plant are stable and reproduced true to type in successive generations.

SUMMARY OF THE INVENTION

Plants of the new *Gaillardia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Dogailspincopsun'. These characteristics in combination distinguish 'Dogailspincopsun' as a new and distinct *Gaillardia* plant:

1. Compact and mounded plant habit.
2. Freely branching habit; dense and bushy habit.
3. Strong leaves that resist yellowing.
4. Early and freely flowering habit.
5. Single inflorescences with red and yellow bi-colored ray florets.
6. Good garden performance.

Plants of the new *Gaillardia* differ primarily from plants of the female parent selection in the following characteristics:

1. Plants of the new *Gaillardia* are more compact, denser and stronger than plants of the female parent selection.
2. Plants of the new *Gaillardia* have stronger and healthier leaves than plants of the female parent selection.

Plants of the new *Gaillardia* can be compared to plants of *Gaillardia* x *grandiflora* 'Sunset Cutie', disclosed in U.S. Plant Pat. No. 26,970. In side-by-side comparisons, plants of the new *Gaillardia* differ from plants of 'Sunset Cutie' in the following characteristics:

1. Plants of the new *Gaillardia* are more compact than and not as vigorous as plants of 'Sunset Cutie'.
2. Plants of the new *Gaillardia* are stronger than plants of 'Sunset Cutie'.

3. Plants of the new *Gaillardia* have stronger and healthier leaves than plants of 'Sunset Cutie'.
4. Plants of the new *Gaillardia* have smaller inflorescences than plants of 'Sunset Cutie'.

BRIEF DESCRIPTION OF THE PHOTOGRAPHS

The accompanying colored photographs illustrate the overall appearance of the new *Gaillardia* plant showing the colors as true as it is reasonably possible to obtain in colored reproductions of this type. Colors in the photographs may differ slightly from the color values cited in the detailed botanical description which accurately describe the colors of the new *Gaillardia* plant.

The photograph on the first sheet is a side perspective view of a typical flowering plant of 'Dogailspincopsun' grown in a container.

The photograph on the second sheet is a close-up view of a typical inflorescence of 'Dogailspincopsun'.

DETAILED BOTANICAL DESCRIPTION

The aforementioned photographs and following observations and measurements describe plants grown in 13-cm containers during the summer in an outdoor nursery in Aalsmeer, The Netherlands and under cultural practices typical of commercial *Gaillardia* production. During the production of the plants, day temperatures averaged 22° C. and night temperatures averaged 17° C. Plants were pinched one time and were three months old when the photographs were taken and 19 weeks old when the description was taken. In the following description, color references are made to The Royal Horticultural Society Colour Chart, 2007 Edition, except where general terms of ordinary dictionary significance are used.

Botanical classification: *Gaillardia aristata* 'Dogailspincopsun'.

Parentage:

*Female, or seed, parent*.—Proprietary selection of *Gaillardia aristata* identified as code number GA13-000001-001, not patented.

*Male, or pollen, parent*.—Unknown selection of *Gaillardia aristata*, not patented.

Propagation:

*Type*.—Terminal vegetative cuttings.

*Time to initiate roots, summer*.—About twelve days at temperatures about 26° C.

*Time to initiate roots, winter*.—About two weeks at temperatures about 23° C.

*Time to produce a rooted young plant, summer*.—About two weeks at temperatures about 23° C.

*Time to produce a rooted young plant, winter*.—About 16 days at temperatures about 18° C.

*Root description*.—Medium in thickness, fibrous; typically white to light brown in color, actual color of the roots is dependent on substrate composition, water quality, fertilizer type and formulation, substrate temperature and physiological age of roots.

*Rooting habit*.—Moderately freely branching, medium density.

Plant description:

*Plant and growth habit*.—Herbaceous perennial; compact and mounded plant habit; moderately vigorous growth habit; moderate growth rate; freely branching habit with about nine primary branches each with about three secondary branches developing per plant; dense and bushy appearance.

*Plant height, soil level to top of foliar plane*.—About 21 cm.

*Plant height, soil level to top of floral plane*.—About 23 cm.

*Plant width*.—About 30 cm.

*Lateral branch description*.—Length: About 19 cm. Diameter: About 5 mm. Internode length: About 1 cm to 3 cm. Strength: Strong. Aspect: Upright to about 30° from vertical. Texture and luster: Pubescent; matte. Color: Close to 139D occasionally tinged with close to 184C.

*Leaf description*.—Arrangement: Alternate, simple; sessile. Length: About 15 cm. Width: About 3.5 cm; if lobes, about 5 cm. Shape: Oblanceolate; occasionally deeply lobed. Apex: Acute. Base: Attenuate to obtuse. Margin: Entire or deeply lobed; ciliate. Texture and luster, upper and lower surfaces: Pubescent; matte. Venation pattern: Pinnate. Color: Developing leaves, upper and lower surfaces: Close to 137C. Fully developed leaves, upper surface: Close to 137C; venation, close to 147D. Fully developed leaves, lower surface: Close to 138A; venation, close to 147D.

Inflorescence description:

*Appearance*.—Single inflorescence form with ray and disc florets; inflorescences held mostly upright on strong peduncles; ray and disc florets develop acropetally on a capitulum.

*Fragrance*.—Faintly fragrant; sweet and pleasant.

*Flowering response*.—Plants begin flowering about eight weeks after planting; plants flower naturally during June and July in The Netherlands.

*Postproduction longevity*.—Inflorescences maintain good substance for about six weeks on the plant; inflorescences not persistent.

*Quantity of inflorescences*.—Freely flowering habit, about 42 inflorescences develop per plant during the flowering season.

*Inflorescence size*.—Diameter: About 9 cm. Disc diameter: About 3 cm.

*Receptacles*.—Height: About 4 mm. Diameter: About 2 cm. Color: Close to 145B.

*Inflorescence buds*.—Height: About 7 mm. Diameter: About 1 cm. Shape: Flattened. Texture and luster: Smooth, glabrous; moderately glossy. Color: Close to 144B to 144C.

*Ray florets*.—Quantity per inflorescence: About 26 to 28 arranged in a single whorl. Length: About 3.5 cm. Width: About 2 cm. Shape: Trumpet-shaped. Apex: Rounded, obtuse. Base: Fused. Margin: Entire; not undulate. Aspect: Horizontal to slightly upright. Texture and luster, upper surface: Smooth, glabrous; matte. Texture and luster, lower surface: Pubescent; matte. Color: When opening, upper surface: Proximally, close to 184B; distally, close to 12A. When opening, lower surface: Proximally, close to 46A; distally, close to 14B. Fully opened, upper surface: Proximally, close to 185B; distally, close to 12A; venation, close to 185B; colors do not change with development. Fully opened, lower surface: Proximally, close to 46A; distally, close to 14B; venation, close to 46A; proximal color becoming closer to 53B with development.

*Disc florets*.—Quantity per inflorescence: About 180 massed at the center of the receptacle in about eight to nine whorls. Length: About 1.5 cm. Diameter: About 2 mm. Shape: Fused tubular. Apex: Acuminate. Texture and luster, inner surface: Smooth, glabrous; moderately glossy. Texture and luster, outer surface: Pubescent; moderately glossy. Color: When opening, inner surface: Close to 185A. When opening, outer surface: Close to 145C. Fully opened, inner surface: Close to 185A; color does not change with development. Fully opened, outer surface: Close to 185C; color does not change with development.

*Involucral bracts*.—Quantity per inflorescence: About 58 arranged in about three to four whorls. Length: About 2.5 cm. Width: About 4 mm. Shape: Lanceolate. Apex: Acute. Base: Truncate. Margin: Entire, ciliate. Texture and luster, upper and lower surfaces: Pubescent, slightly rough; matte. Color, upper and lower surfaces: Close to 137C.

*Peduncles*.—Length: About 22 cm. Diameter: About 3 mm to 4 mm. Strength: Strong. Texture and luster: Pubescent; slightly glossy. Color: Close to 138C.

*Reproductive organs*.—Androecium: Present on disc florets only. Quantity per floret: Five. Filament length: About 5 mm. Filament color: Close to 150D. Anther length: About 4 mm. Anther shape: Rectangular. Anther color: Close to 13B; upper surface, darker than 187A. Pollen amount: Abundant. Pollen color: Close to 14A. Gynoecium: Present on disc florets only. Quantity per floret: One. Pistil length: About 1.4 cm. Stigma diameter: About 1 mm. Stigma shape: Two-lobed, plumose. Stigma color: Close to 187B. Style length: About 7 mm. Style color: Close to 157C. Ovary color: Close to 149D.

*Seeds and fruits*.—To date, seed and fruit production have not been observed on plants of the new *Gaillardia*.

Pathogen & pest resistance: To date, plants of the new *Gaillardia* have not been observed to be resistant to pathogens and pests common to *Gaillardia* plants.

Garden performance: Plants of the new *Gaillardia* have been observed to have good garden performance and to tolerate wind and rain and temperatures ranging from −15° C. to 35° C.

It is claimed:

1. A new and distinct *Gaillardia* plant named 'Dogailspincopsun' as illustrated and described.

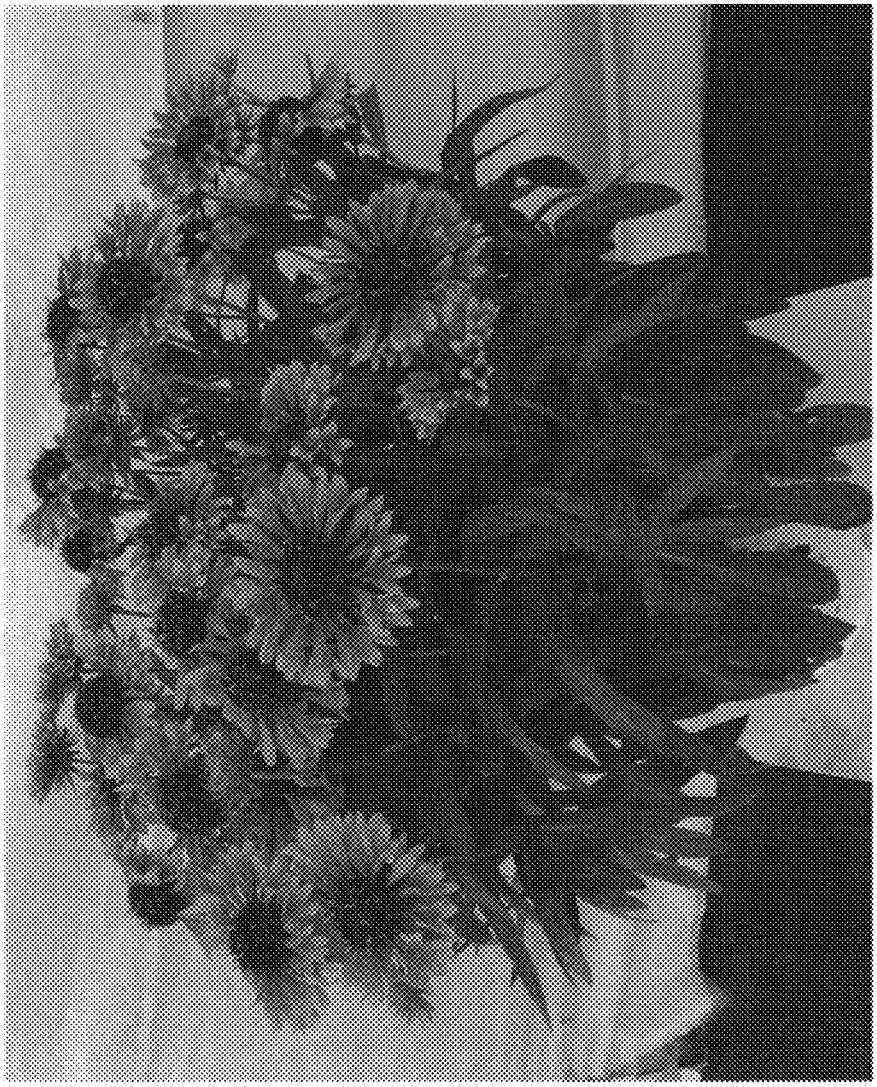

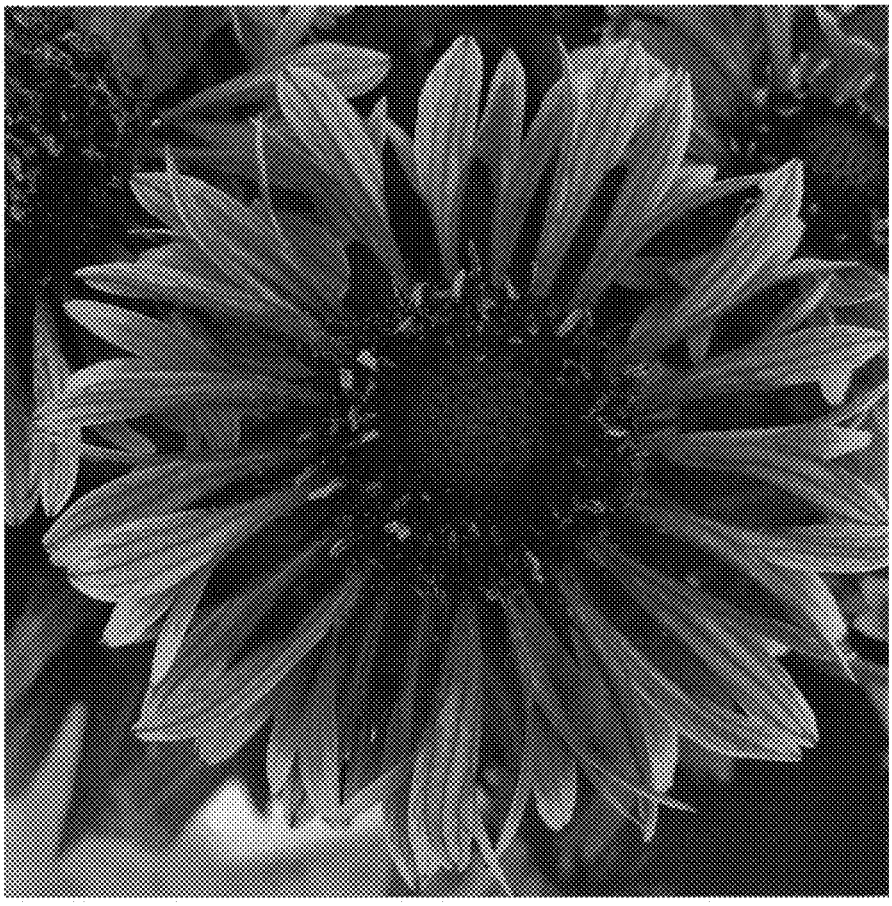

* * * * *